United States Patent [19]

Kushner et al.

[11] 4,033,482
[45] July 5, 1977

[54] CONICAL LIQUID METERING DEVICE

[75] Inventors: Jack Kushner, Lindenhurst; Henry G. Zwirblis, Nesconset, both of N.Y.

[73] Assignee: Delta Scientific Corporation, Lindenhurst, N.Y.

[22] Filed: Nov. 20, 1975

[21] Appl. No.: 633,856

Related U.S. Application Data

[62] Division of Ser. No. 501,875, Aug. 30, 1974, Pat. No. 3,999,945.

[52] U.S. Cl. .............................. 222/136; 222/139; 222/194; 222/370
[51] Int. Cl.² .......................................... B67D 5/52
[58] Field of Search .......... 222/139, 194, 216, 217, 222/218, 136, 370, 250

[56] References Cited
UNITED STATES PATENTS

| | | | |
|---|---|---|---|
| 2,427,680 | 9/1947 | Leonard | 222/250 X |
| 3,273,758 | 9/1966 | Starrett | 222/194 |
| 3,610,476 | 10/1971 | Starrett | 222/194 |
| 3,750,902 | 8/1973 | Starrett | 222/194 |

Primary Examiner—Allen N. Knowles
Attorney, Agent, or Firm—Pennie & Edmonds

[57] ABSTRACT

A device for precisely metering out quantities of fluids is disclosed. The device comprises a tapered rotor having a plurality of chambers, each of the chambers having first and second openings. The rotor is received within a housing and together with the housing cooperates to perform the metering function as the rotor is rotated with respect to the housing. The housing has a plurality of input and overflow ports corresponding to the chambers in the rotor. These ports are positioned with respect to the rotor in such a manner that when a corresponding input port is in communication with one of said openings, its corresponding overflow port is in communication with the other of said openings. The housing also comprises a plurality of pressure ports and output ports which correspond to the plurality of chambers. The pressure and output ports are positioned in such a manner that when one opening of a chamber is in communication with its corresponding pressure port, its other opening is in communication with its output port.

11 Claims, 5 Drawing Figures

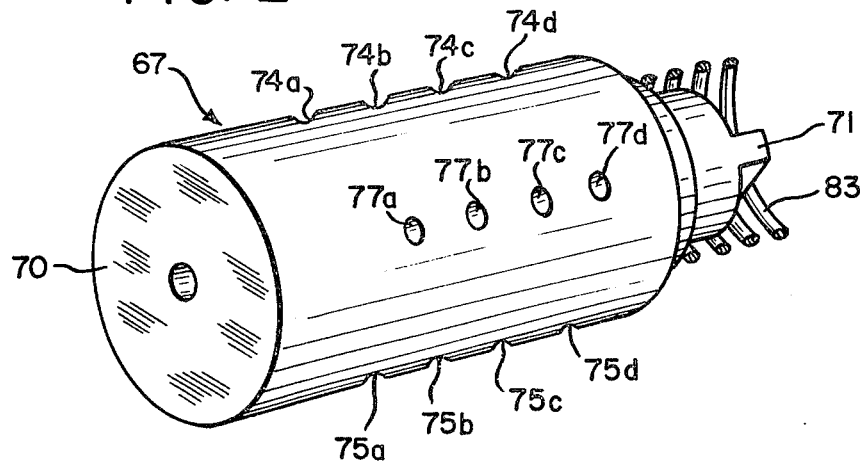
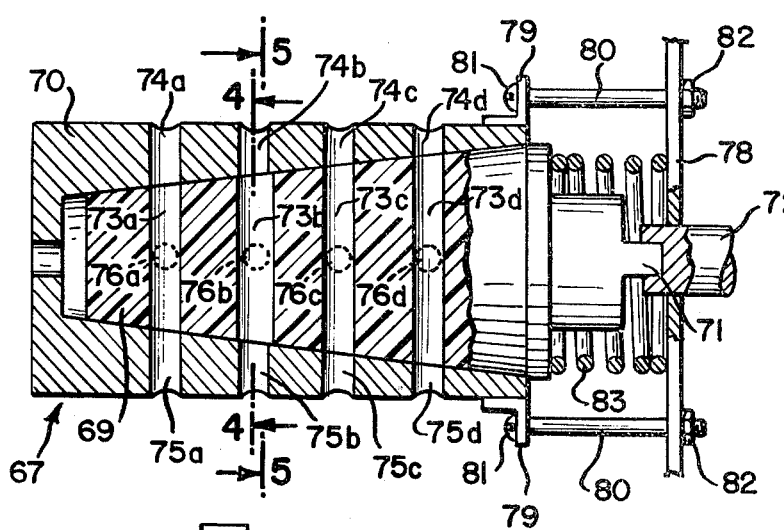
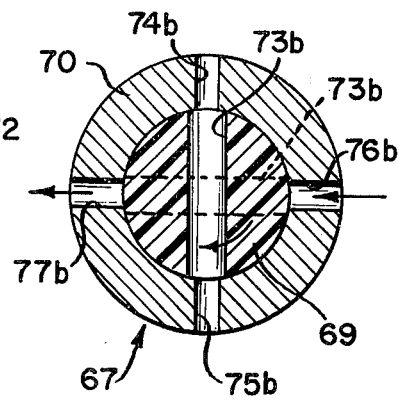
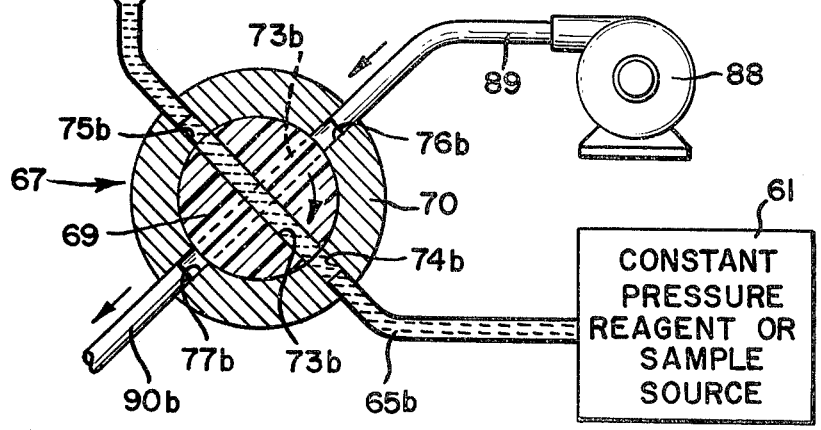

CONICAL LIQUID METERING DEVICE

CROSS-REFERENCE TO RELATED APPLICATION

This application is a divisional of our copending United States Patent Application Ser. No. 501,875 filed Aug. 30, 1974, now U.S. Pat. No. 3,999,945 entitled "Liquid Analysis System".

BACKGROUND OF THE INVENTION

With increasing public concern over the quality of the environment, a significant need has arisen for equipment which is capable of accurately and economically monitoring various environmental conditions. The present invention, while particularly suitable for employment in automated chemical analysis equipment monitoring the quantity of pollutant in a body of water, such as a lake, stream or municipal water supply, is generally useful for continuously and automatically providing measured quantities of liquids in any system.

Conventionally, if one wishes to measure the level of pollutant, the biological oxygen demand or some other parameter of a body of water, one takes a sample of the water and submits it to an appropriate quantitative chemical analysis. These chemical tests generally comprise a number of steps involving the mixing and reacting of a predetermined amount of the sample or reacted sample with specific quantities of various chemical reagents.

These tests are best carried out individually by relatively highly skilled personnel. Naturally, if one wishes to use a test to obtain data continuously or at frequent intervals and thus construct an accurate and complete picture of the state of water quality over a period of time, conventional manual testing is quite expensive.

SUMMARY OF THE INVENTION

The present invention is directed toward an apparatus for continuously and automatically producing discrete predetermined quantities of liquids for use in an automatic quantitative chemical analysis. The metering device of the present invention is particularly useful in the performance of water quality tests in an automated or semiautomated system requiring the metering out of accurately controlled quantities of testing reagents. The metering device of the present invention can also be advantageously employed in other apparatus requiring a highly precise metering operation.

In accordance with the present invention, metering is performed by a frustroconical rotor which has a plurality of radially disposed bores along its length. The rotor is disposed in a housing whose inner surface mates with the frustroconical shape of the rotor. The housing has first and second sets of radially disposed pairs of ports along its length. Each pair of ports of one of the sets is positioned in the housing in such a manner that each of the ports of a given port pair lines up with one of the end openings of one of the bores when the rotor is in a given position. The other set of pairs of ports is aligned with the bores when the rotor is in a second position.

During operation, the rotor is rotated in the housing. One of each of the first set of pairs of ports is coupled to a source of reagent and sample of the water to be tested. As the bores in the rotor become aligned with the first set of pairs of ports in the housing, liquid is caused to flow through one of each of the pairs of those ports, thereby filling the bores. For example, with a rotor having four bores, one may be filled with sample water and the other three with different reagents. Attached to the other port of each pair is a tube of sufficient height in relation to the pressure of the source as to receive the excess liquid without overflow. As the rotor continues to rotate, the filled bores come into alignment with the second set of pairs of ports. One of the ports of each pair of ports of this set is connected to a blower which, as the bores and the ports begin to align, blows the reagent that has filled the bores through the opposite end opening of each bore and into the aligned port of the housing which serves as an output.

The amount of sample water and reagent collected by the metering apparatus is a function of the volume of the bores in the rotor. It is advantageously to feed the reagents and the sample water to the metering device at the same pressures. This prevents migration of a liquid from one of the pairs of bores or ports to another due to a difference in pressure head between the pairs. Although, in the described embodiment, all of the bores are filled and emptied simultaneously, the pattern can be varied by appropriate radial placement of the bores or ports to achieve other sequencing characteristics.

BRIEF DESCRIPTION OF THE DRAWINGS

FIG. 2 is a perspective view of the metering device of the present invention;

FIG. 3 is a view, partially in section, of the device illustrated in FIG. 2;

FIG. 4 is a cross-sectional view along line 4—4 of FIG. 3; and

FIG. 5 is a cross-sectional view along line 5—5 of FIG. 3 including a schematic illustration of the principle components of the system.

DETAILED DESCRIPTION OF THE PREFERRED EMBODIMENTS

Figure 1:
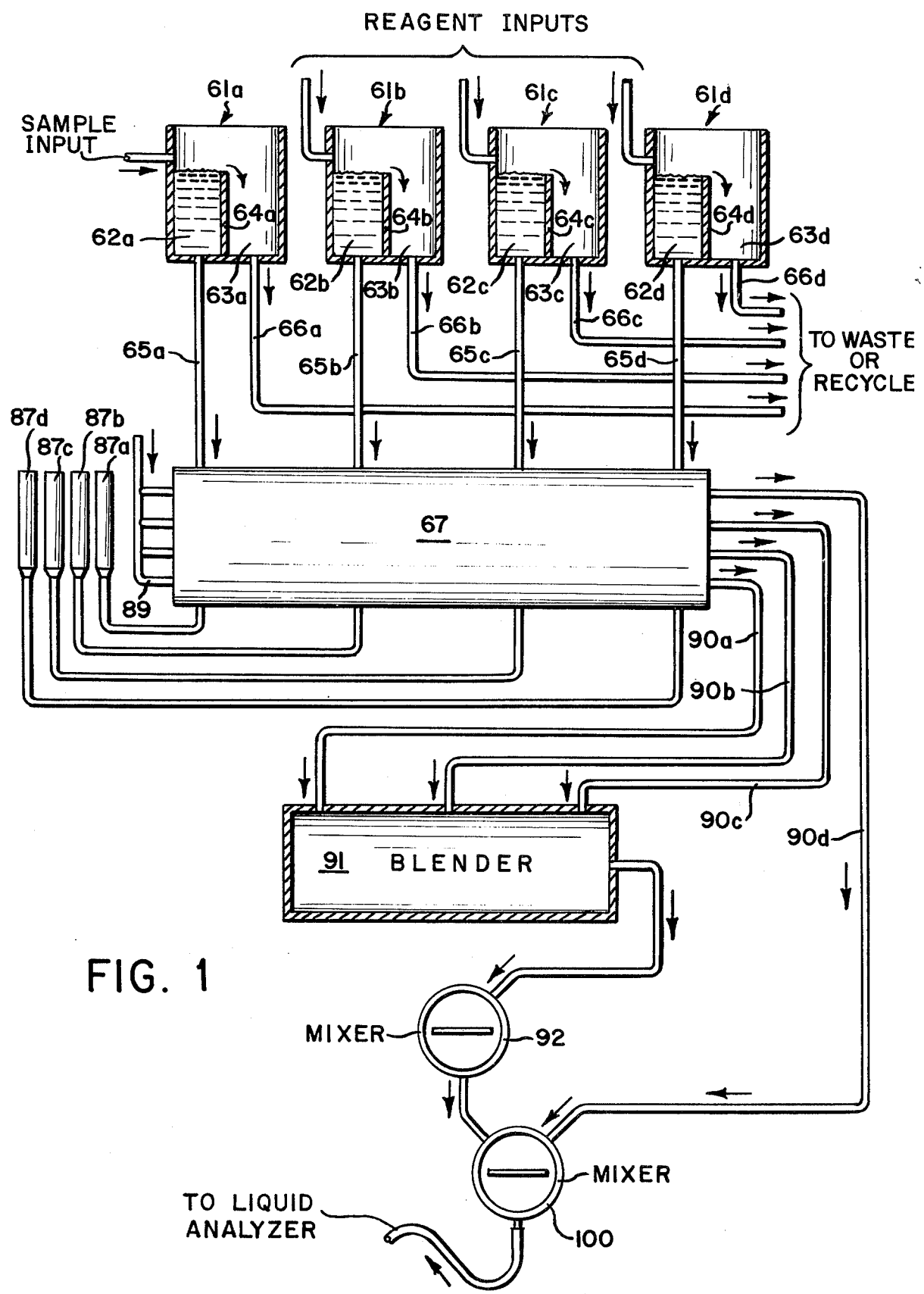
FIG. 1 is a flow diagram of an automatic analyzer apparatus incorporating the metering device of the present invention.

Referring to FIG. 1, a portion of a sampled liquid either from the centrifuge or directly from the sampling device is sent to constant pressure liquid source 61a. A set of constant pressure sources 61a–d comprises a plurality of sources corresponding to the sample liquid to be tested and the reagents to be used in the reaction. Each constant pressure source is divided into two cells 62a–d and 63a–d. Liquid from the sample source and the other reagent sources enters cells 62a–d and fills each to the top of center dividers 64a–d. The tops of all the center dividers are at the same level. Hence, the pressure at the bottom of each of the cells 62a–d is uniform, as a consequence of the fact that each of the output conduits 65a–d sees the same height of liquid above it. This results in a constant pressure at the output of conduits 65a–d which are of uniform height leading from constant pressure source 61. Overflow from cells 62a–d is received into cells 63a–d and exits through drain conduits 66a–d. The drained portion of the sample or reagents may either be wasted or recycled. The output conduits 65a–d are coupled to metering unit 67.

As illustrated in FIGS. 2–4, the metering device 67 of the present invention comprises a tapered rotor 69 in a housing 70. Rotor 69 includes an extension 71 to which a source of motive power such as motor shaft 72 is coupled, thus allowing the rotor to be rotated. A plurality of bores 73a–d are disposed in rotor 69. The bores define liquid receiving chambers and their volume is chosen to be equal to the quantity of liquid which one wishes to meter out. The device 67 is positioned so that the average height of each bore is the same distance below the output ports of the constant pressure sources 61a–d. As can be seen most clearly in FIG. 3, one end opening of each bore 73a–d lines up with corresponding liquid feeding ports 74a–d in housing 70 when rotor 69 is in a first angular position with respect to the housing. In this first position, the ports 74a–d are coupled to conduits 65a–d on one side of the bores 73a–d while the other end openings of the bores are connected to reagent overflow ports 75a–d. At a second angular position, bores 73a–d are in alignment with pressure ports 76a–d and output ports 77a–d. In FIG. 4, this second position is shown in phantom lines for the bore 73b.

Housing 70 may be supported on any surface 78 of the apparatus in which it is to be used. A typical support may comprise a number of brackets 79 secured to the outer periphery of the housing and supported on surface 78 by a corresponding number of sleeves 80 which are secured to the brackets and surface 78 by bolts and nuts 82.

The use of a tapered, conically shaped, rotor and housing is particularly advantageous due to the fact that such a configuration does not require very precise machining during manufacture. It is also noted that the rotor may be made of a plastic material, such as that sold under the trademark TEFLON, which is softer than the housing and which, with use, tends to conform in shape to the shape of the inside mating surface of the housing and thus minimize leakage. Leakage can be effectively eliminated by using a spring 83 to urge the rotor into the housing.

The angle of the taper in the frustroconical rotor has also been found to be important. Specifically, if the taper is relatively shallow, jamming tends to occur as the spring urges the rotor into the housing. If, on the other hand, the taper is made too steep, leakage becomes a problem, and an extremely strong spring is needed to prevent leakage. In practice, it has been found that a taper of approximately 6° from the axis of rotation functions quite satisfactorily for most applications, although any angle in the range between 2° and 10° will work with varying degrees of success.

The operation of the metering device illustrated in FIGS. 2–4 is schematically illustrated in FIG. 5. For simplicity of illustration, only the connections associated with a single bore 73b have been shown. The system includes a plurality of conduits 65 which receive liquid sample or reagent from the constant pressure sources 61 which feed the sample and the reagents to the metering device 67. Each of the liquids is fed to the metering device with the same pressure in order that the migration of reagents between the input ports 74a–d at the interface between rotor 69 and housing 70 is minimized.

Due to the nature of the arrangement, such feeding is made with relatively little turbulence, thereby achieving a high degree of uniformity in the filling operation. During filling, after the reagent or liquid has filled the bore, it proceeds through overflow ports 75a–d and into overflow tubes 87. The volume of reagent liquid in bores 73a–d is, therefore, equal to the volume of the bore. Overflow tubes 87 are also filled with liquid to a height dependent upon the pressure with which the liquid reagent is fed to the metering device 67.

As the rotor 69 continues to turn with respect to the housing 70, it comes to the position shown in phantom lines in FIG. 5. In this position, a blower 88 blows air through a conduit 89 to pressure ports 76a–d, thereby driving the volume of reagent in bores 73a–d through output ports 77a–d and output conduits 90. In this manner, predetermined discrete volumes of liquid reagent or liquid to be tested are metered out in discrete fashion. Naturally, if one desired to do so, one could vary the sequence of feeding by variation of the position of the bores and ports.

The output of the metering device may then be sent to any combination of blenders 91 and mixers 92, 100 and onto a liquid analyzer which would be appropriate for carrying out the quantitative analysis which one wishes to perform. Such a system is disclosed in our copending United States Patent Application Ser. No. 501,875 filed Aug. 30, 1974, now U.S. Pat. No. 3,999,945, entitled "Liquid Analysis System".

We claim:

1. A device for precisely metering out quantities of fluid, comprising:
   a. a tapered rotor having a chamber having first and second openings which are in fluid communication with each other;
   b. a mating housing for receiving said rotor, said housing having:
      1. an input port for communicating with one opening of said chamber when said rotor is in a first position with respect to said housing,
      2. an overflow port for communicating with the other opening when said input port is in communication with said one opening,
      3. a pressure port for communicating with one opening when said rotor is in a second position with respect to said housing, and
      4. an output port for communicating with the other opening when said pressure port is in communication with said one opening; and
   c. overflow receiving means connected to said overflow port.

2. A device according to claim 1 wherein:
   a. said tapered rotor is of a conical shape and said housing has a mating control surface.

3. A device according to claim 2 wherein:
   a. said chamber is a bore which extends radially through said rotor.

4. A device according to claim 2 further comprising:
   a. a spring for urging said rotor into said housing.

5. A device according to claim 1 wherein:
   a. said rotor is made of a material which is softer than the material of which said housing is made.

6. A device according to claim 6 wherein:
   a. said material is plastic.

7. A device for precisely metering out quantities of fluids comprising:
   a. a tapered rotor having a plurality of chambers, each of said chambers having first and second openings which are in fluid communication with each other;
   b. a mating housing for receiving said rotor, said housing having:
      1. a plurality of corresponding input ports, each for communicating with one opening in its corresponding chamber when said rotor is in a first position,
      2. a plurality of corresponding overflow ports, each for communicating with the other opening of its corresponding chamber when the corresponding input port is in communication with said one opening of its corresponding chamber,
3. a plurality of corresponding pressure ports, each for communicating with one opening in its corresponding chamber when said rotor is in a second position with respect to said housing, and
4. a plurality of corresponding output ports, each for communicating with the other opening of its corresponding chamber when its corresponding pressure port is in communication with said one opening of its corresponding chamber; and
c. overflow receiving means connected to said overflow ports.

8. A device according to claim 7 wherein:

a. said tapered rotor has a conical shape and said housing has a mating conical surface.

9. A device according to claim 8 wherein:

a. each of said chambers is a bore which extends radially through said rotor.

10. A device according to claim 7 further comprising:

a. a means for supplying a corresponding fluid to each of said input ports; and
b. means for applying pressure to said plurality of pressure ports.

11. A device according to claim 8 wherein:

a. the conical shaped rotor has an outer surface that diverges from the axis of rotation of the cone by an angle within the range of 2° to 10°.

* * * * *

UNITED STATES PATENT AND TRADEMARK OFFICE
CERTIFICATE OF CORRECTION

PATENT NO. : 4,033,482
DATED : July 5, 1977
INVENTOR(S) : Jack Kushner and Henry G. Zwirblis It is certified that error appears in the above-identified patent and that said Letters Patent are hereby corrected as shown below:

Column 2, line 15, "advantageously" shoud read --advantageous--.

Column 4, line 22, "fluid" should read --fluids--;

line 44, "control surface" should read --conical surface--;

line 53, "to claim 6" should read --to claim 5--.

Signed and Sealed this

First Day of November 1977

[SEAL]

Attest:

RUTH C. MASON
Attesting Officer

LUTRELLE F. PARKER
Acting Commissioner of Patents and Trademarks